United States Patent
Ahn et al.

(10) Patent No.: US 8,771,193 B2
(45) Date of Patent: Jul. 8, 2014

(54) CANAL TYPE MINI-APPARATUSES INSERTABLE IN EARS FOR DIAGNOSING AND CURING DISEASES

(75) Inventors: Chang-Geun Ahn, Daejeon (KR); Sooyeul Lee, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 90 days.

(21) Appl. No.: 13/356,529

(22) Filed: Jan. 23, 2012

(65) Prior Publication Data

US 2012/0253166 A1 Oct. 4, 2012

(30) Foreign Application Priority Data

Apr. 1, 2011 (KR) .................. 10-2011-0030254

(51) Int. Cl.
*A61B 8/14* (2006.01)

(52) U.S. Cl.
USPC ............ 600/459; 600/473; 600/476; 600/478

(58) Field of Classification Search
USPC .................. 600/473–480, 437–469
See application file for complete search history.

(56) References Cited

U.S. PATENT DOCUMENTS

| | | | |
|---|---|---|---|
| 7,277,744 B2 | 10/2007 | Schaefer et al. | |
| 7,652,259 B2 | 1/2010 | Kimchy et al. | |
| 8,328,420 B2 * | 12/2012 | Abreu | 374/208 |
| 2006/0217632 A1 * | 9/2006 | Causevic et al. | 600/559 |
| 2009/0030295 A1 * | 1/2009 | Shioi et al. | 600/316 |
| 2009/0185191 A1 * | 7/2009 | Boppart et al. | 356/479 |
| 2010/0185115 A1 * | 7/2010 | Causevic et al. | 600/544 |
| 2012/0071824 A1 * | 3/2012 | Chang et al. | 604/96.01 |
| 2013/0027515 A1 * | 1/2013 | Vinther et al. | 348/44 |

OTHER PUBLICATIONS

U. Bollag et al., "The use of acoustic reflectometry in the study of middle ear effusion in children suffering from acute otits media, upper respiratory tract infection and in healthy children", Eur J Pediatr, 1996, pp. 1027-1030, vol. 155, Springer-Verlag.

Mark F. Spire et al., "Use of infrared thermography to detect inflammation caused by contaminated growth promotant ear implants in cattle", Journal of the American Veterinary Medical Association, Nov. 1, 1999, pp. 1320-1324, vol. 215 No. 9, JAVMA.

* cited by examiner

*Primary Examiner* — Sanjay Cattungal

(57) ABSTRACT

Provided is a canal type mini-apparatus insertable in an ear for diagnosing a disease. The canal type mini-apparatus includes a canal body and a protrusion body. The canal body is insertable in an ear and includes a bio-data detection unit at an end thereof. The bio-data detection unit is configured to detect biological data from an inside of the ear for diagnosing a disease. The protrusion body is disposed at the other end of the canal body and including a data transceiving unit. The data transceiving unit is configured to control the bio-data detection unit and transmit/receive a signal to/from an analyzing device. When the canal type mini-apparatus is inserted in the ear, at least a portion of the protrusion body protrudes outward from the ear.

8 Claims, 4 Drawing Sheets

CANAL TYPE MINI-APPARATUSES INSERTABLE IN EARS FOR DIAGNOSING AND CURING DISEASES

CROSS-REFERENCE TO RELATED APPLICATIONS

This U.S. non-provisional patent application claims priority under 35 U.S.C. §119 of Korean Patent Application No. 10-2011-0030254, filed on Apr. 1, 2011, the entire contents of which are hereby incorporated by reference.

BACKGROUND OF THE INVENTION

The present invention disclosed herein relates to canal type mini-apparatuses insertable in ears for diagnosing and curing diseases, and more particularly, to canal type mini-apparatuses insertable in ears for determining the degrees and developments of diseases and curing the diseases.

In hospitals, ear diseases are diagnosed by observing images taken from the inside of an ear by using imaging apparatuses.

For example, a doctor diagnoses tympanitis (otitis media) based on his/her experience and knowledge after observing the inside of an ear using endoscope equipment which is generally immobile.

Since expensive equipment such as endoscope equipment is used, such diseases cannot be easily diagnosed outside the hospital. Therefore, it is difficult for ordinary persons to early find their diseases such as tympanitis (otitis media) and analyze the progress of tympanitis.

SUMMARY OF THE INVENTION

The present invention provides canal type mini-apparatuses insertable in ears for determining the degrees and developments of diseases and curing the diseases.

The object of the present invention is not limited to the aforesaid, but other objects not described herein will be clearly understood by those skilled in the art from descriptions below.

Embodiments of the present invention provide canal type mini-apparatuses insertable in an ear for diagnosing a disease, the canal type mini-apparatus including: a canal body insertable in an ear and including a bio-data detection unit at an end thereof, the bio-data detection unit being configured to detect biological data from an inside of the ear for diagnosing a disease; and a protrusion body disposed at the other end of the canal body and including a data transceiving unit, the data transceiving unit being configured to control the bio-data detection unit and transmit/receive a signal to/from an analyzing device, wherein when the canal type mini-apparatus may be inserted in the ear, at least a portion of the protrusion body protrudes outward from the ear.

In some embodiments, the analyzing device may be disposed in the protrusion body.

In other embodiments, the analyzing device may be a separate external analyzing device. The analyzing device may be connected to the data transceiving unit through a wired or wireless communication link.

In even other embodiments, the bio-data detection unit may be configured to capture an image from an inner skin of the ear for diagnosing at least one of tympanitis, tympanum trouble, and jaundice.

In yet other embodiments, the bio-data detection unit may include: an image capture unit configured to capture an image of the inner skin of the ear; a data processing unit configured to convert the image into a transmission signal; and a data transmitting unit configured to transmit the transmission signal to the analyzing device.

In further embodiments, the image capture unit may include at least one set of a set of an optical source and an image sensor and a set of an ultrasonic generator and an ultrasonic detector.

In still further embodiments, the set of the optical source and the image sensor may be configured to capture one of a still image, a video, and a heat distribution image from a surface of the inner skin of the ear.

In even further embodiments, the set of the ultrasonic generator and the ultrasonic detector may be configured to capture ultrasonic images from a surface and an inside of the inner skin of the ear.

In yet further embodiments, the bio-data detection unit may be configured to detect a basic biological signal including at least one of temperature, pulse, blood pressure, and electrocardiogram.

In some embodiments, the canal body may further include a medium injection unit disposed at the end of the canal body and configured to generate a medium to cure the disease of the ear.

In other embodiments, if the analyzing device diagnoses a disease based on biological data detected from the inside of the ear by the bio-data detection unit and transmits a medium-request signal, the medium injection unit may generate the medium for curing the disease.

In still other embodiments, the medium injection unit may include: a data receiving unit configured to receive a transmission signal providing information about a diagnosed disease from the analyzing device; a medium control unit configured to select a medium suitable for curing the diagnosed disease based on the transmission signal; and a medium generating unit configured to generate the medium selected by the medium control unit.

In even other embodiments, the medium generating unit may include at least one of a far-infrared generator, a heat generator, an ultrasonic generator, and a plasma generator.

In yet other embodiments, the protrusion body may have a socket or adaptor shape for coupling with the canal body.

In other embodiments of the present invention, there are provided canal type mini-apparatuses insertable in an ear for curing a disease, the canal type mini-apparatus including: a canal body insertable in an ear and including a medium injection unit at an end thereof, the medium injection unit being configured to generate a medium to an inside of the ear for curing a disease; and a protrusion body disposed at the other end of the canal body and including a data receiving unit, the data receiving unit being configured to control the medium injection unit and receive a signal from an analyzing device, wherein when the canal type mini-apparatus may be inserted in the ear, at least a portion of the protrusion body protrudes outward from the ear.

In some embodiments, the analyzing device may be disposed in the protrusion body.

In other embodiments, the analyzing device may be a separate external analyzing device. The analyzing device may be connected to the data receiving unit through a wired or wireless communication link.

In even other embodiments, the medium injection unit may include: a data receiving unit configured to receive a transmission signal providing information about a diagnosed disease from the analyzing device; a medium control unit configured to select a medium suitable for curing the diagnosed disease based on the transmission signal; and a medium generating unit configured to generated the medium selected by the medium control unit.

In yet other embodiments, the medium generating unit may include at least one of a far-infrared generator, a heat generator, an ultrasonic generator, and a plasma generator.

In further embodiments, the canal body may further include a bio-data detection unit disposed at the end of the canal body and configured to detect biological data from the inside of the ear for diagnosing the disease.

In still further embodiments, the bio-data detection unit may be configured to capture an image from an inner skin of the ear for diagnosing at least one of tympanitis, tympanum trouble, and jaundice.

In even further embodiments, the bio-data detection unit may include: an image capture unit configured to capture an image of the inner skin of the ear; a data processing unit configured to convert the image into a transmission signal; and a data transmitting unit configured to transmit the transmission signal to the analyzing device.

In yet further embodiments, the image capture unit may include at least one set of a set of an optical source and an image sensor and a set of an ultrasonic generator and an ultrasonic detector.

In some embodiments, the set of the optical source and the image sensor may be configured to capture one of a still image, a video, and a heat distribution image from a surface of the inner skin of the ear.

In other embodiments, the set of the ultrasonic generator and the ultrasonic detector may be configured to capture ultrasonic images from a surface and an inside of the inner skin of the ear.

In still other embodiments, the bio-data detection unit may be configured to detect a basic biological signal including at least one of temperature, pulse, blood pressure, and electrocardiogram.

In even other embodiments, the protrusion body may have a socket or adaptor shape for coupling with the canal body.

In still other embodiments of the present invention, there are provided canal type mini-apparatuses insertable in an ear for diagnosing and curing a disease, the canal type mini-apparatus including: a canal body insertable in an ear and including a bio-data detection unit and a medium injection unit at an end thereof, the bio-data detection unit being configured to detect biological data from an inside of the ear for diagnosing a disease, the medium injection unit being configured to generate a medium to the inside of the ear for curing the diagnosed disease; and a protrusion body disposed at the other end of the canal body and including a data transceiving unit, the data transceiving unit being configured to control the bio-data detection unit and the medium injection unit and transmit/receive a signal to/from an analyzing device, wherein when the canal type mini-apparatus may be inserted in the ear, at least a portion of the protrusion body protrudes outward from the ear.

BRIEF DESCRIPTION OF THE DRAWINGS

The accompanying drawings are included to provide a further understanding of the present invention, and are incorporated in and constitute a part of this specification. The drawings illustrate exemplary embodiments of the present invention and, together with the description, serve to explain principles of the present invention. In the drawings.

DETAILED DESCRIPTION OF PREFERRED EMBODIMENTS

Figure 1:
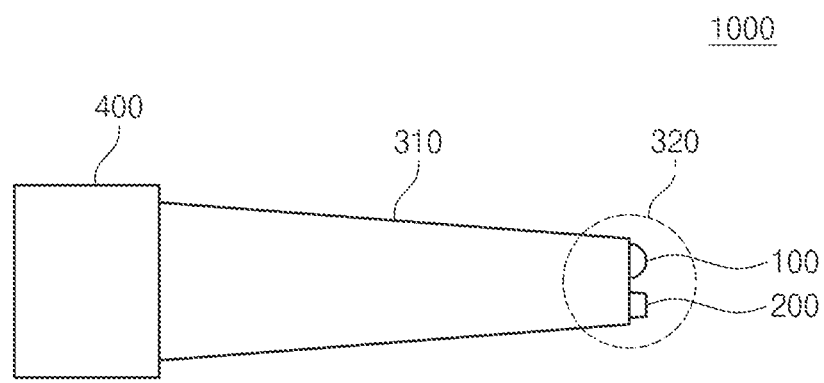
FIG. 1 is a schematic diagram illustrating a canal type mini-apparatus insertable in an ear for diagnosing and curing diseases according to an embodiment of the present invention.

Exemplary embodiments of the present invention will be described below in more detail with reference to the accompanying drawings. Advantages and features of the present invention, and implementation methods thereof will be clarified through following embodiments described with reference to the accompanying drawings. The present invention may, however, be embodied in different forms and should not be constructed as limited to the embodiments set forth herein. Rather, these embodiments are provided so that this disclosure will be thorough and complete, and will fully convey the scope of the present invention to those skilled in the art. Further, the present invention is only defined by scopes of claims. Like reference numerals refer to like elements throughout the present disclosure.

In the following description, technical terms are used only for explaining specific embodiments while not limiting the present invention. The terms of a singular form may include plural forms unless otherwise specified. Also, the meaning of "include," "comprise," "including," or "comprising," specifies a property, a region, a fixed number, a step, a process, an element and/or a component but does not exclude other properties, regions, fixed numbers, steps, processes, elements and/or components. Since exemplary embodiments are provided below, the order of the reference numerals given in the description is not limited thereto.

In addition, exemplary embodiments of the present invention in the detailed description will be described with reference to sectional views and/or plan views as ideal exemplary views of the present invention. In the drawings, the dimensions of layers and regions are exaggerated for clarity of illustration. Accordingly, shapes of the exemplary views may be modified according to manufacturing techniques and/or allowable errors. Therefore, the embodiments of the present invention are not limited to the specific shape illustrated in the exemplary views, but may include other shapes that may be created according to manufacturing processes. Elements exemplified in the drawings have general properties, and are used to illustrate a specific shape of an apparatus. Thus, this should not be construed as limiting the present invention.

Figure 2:
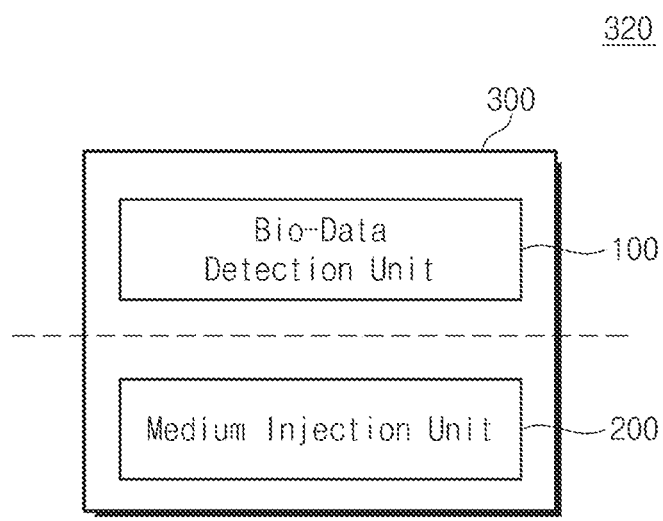
FIG. 2 is a block diagram illustrating a diagnosis and curing unit of the canal type mini-apparatus according to an embodiment of the present invention.

FIG. 1 is a schematic diagram illustrating a canal type mini-apparatus 1000 insertable in an ear for diagnosing and curing diseases according to an embodiment of the present invention; FIG. 2 is a block diagram illustrating a diagnosis and curing unit 300 of the canal type mini-apparatus 1000 according to an embodiment of the present invention; and FIG. 3 is a schematic diagram illustrating the canal type mini-apparatus 1000 inserted in an ear according to an embodiment of the present invention.

Figure 3:
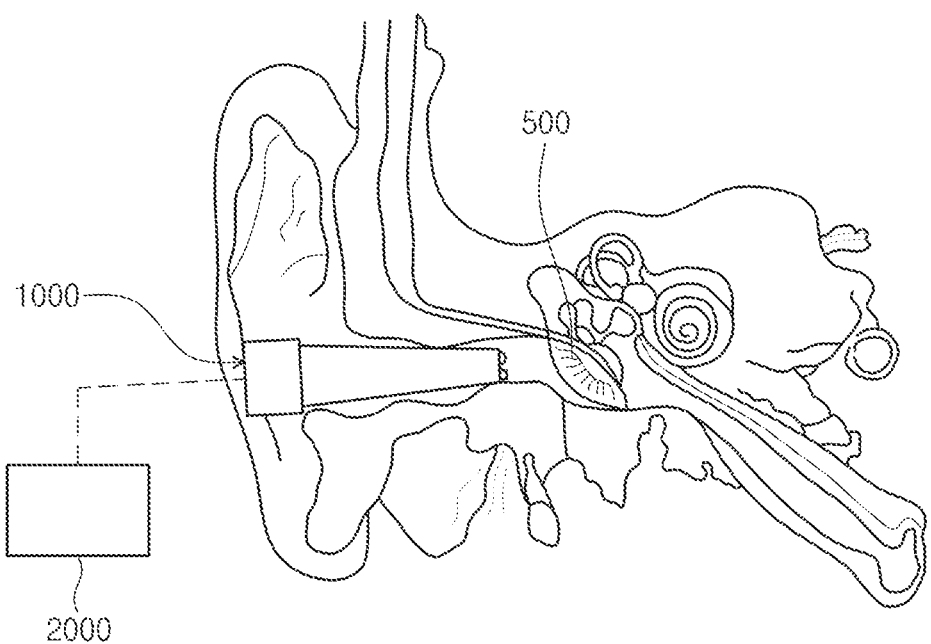
FIG. 3 is a schematic diagram illustrating the canal type mini-apparatus inserted in an ear according to an embodiment of the present invention.

Referring to FIGS. 1 through 3, the canal type mini-apparatus 1000 is insertable in an ear for diagnosing and curing diseases. The canal type mini-apparatus 1000 may include: a canal end 320 including a bio-data detection unit 100 and a medium injection unit 200; a canal body 310 insertable in the ear; and a protrusion body 400 protruding outward when the canal type mini-apparatus 1000 is inserted in the ear.

The bio-data detection unit 100 and the medium injection unit 200 are small so that when the canal type mini-apparatus 1000 is inserted in the ear, the bio-data detection unit 100 and the medium injection unit 200 can be placed in a deep position of the ear. For example, the canal end 320 may be inserted to the middle ear in front of a tympanic membrane 500.

As shown in FIG. 3, the canal body 310 may have a canal shape so that the canal body 310 can be easily inserted in the ear with less discomfort. In addition, the canal body 310 may be coated with a flexible material.

A unit such as a data transceiving unit (refer to a data transmitting unit 160 of FIG. 4 or a data receiving unit 260 of FIG. 5) may be disposed in the protrusion body 400 to control the bio-data detection unit 100 and the medium injection unit 200 and transmit/receive signals to/from an analyzing device 2000. The analyzing device 2000 analyzes biological data (biological signals) and displays the analysis results. The protrusion body 400 may be connected to the analyzing device 2000 by a wired or wireless communication link so as to transmit the biological signals (biological data) to the analyzing device 2000. In some cases, the protrusion body 400 may be provided in one piece with the analyzing device 2000 that analyzes the biological signals (biological data) and displays the analysis results. In other cases, the protrusion body 400 may be provided in the form of a socket or adapter to which the canal body 310 can be coupled. In these cases, another ear-insertable device having another function may be coupled to the protrusion body 400 instead of the canal body 310.

The canal end 320 of the canal type mini-apparatus 1000 may include the diagnosis and curing unit 300 constituted by the bio-data detection unit 100 configured to detect biological data from a user and the medium injection unit 200 configured to generate a medium and inject the medium into the ear of the user for improving the health of the user.

The bio-data detection unit 100 takes images of an inner skin of the ear and transmits the image to the external analyzing device 2000 for diagnosing diseases such as tympanitis (otitis media), tympanum trouble, and jaundice. Still images, videos, or heat distribution images may be obtained using an image sensor 120 (refer to FIG. 4). A beam may be cast from an optical source 110 (refer to FIG. 4) for obtaining an image having a better quality. In addition to the image sensor 120, an ultrasonic generator 140 (refer to FIG. 4) and an ultrasonic detector 130 (refer to FIG. 4) may be used to obtain biological images from the surface, inside, and tissues of the inner skin of the ear. In addition, a basic bio-signal detection sensor may be used to detect biological signals such as temperature, pulse, blood pressure, and electrocardiogram.

The medium injection unit 200 may generate a medium such as infrared rays, heat, ultrasonic waves, and plasma and inject the medium into the ear of the user to improve the health of the user. For example, if a doctor determines that far-infrared radiation treatment is necessary for an otitis media patient, the patient may receive far-infrared radiation treatment at home by using the canal type mini-apparatus 1000.

Figure 4:
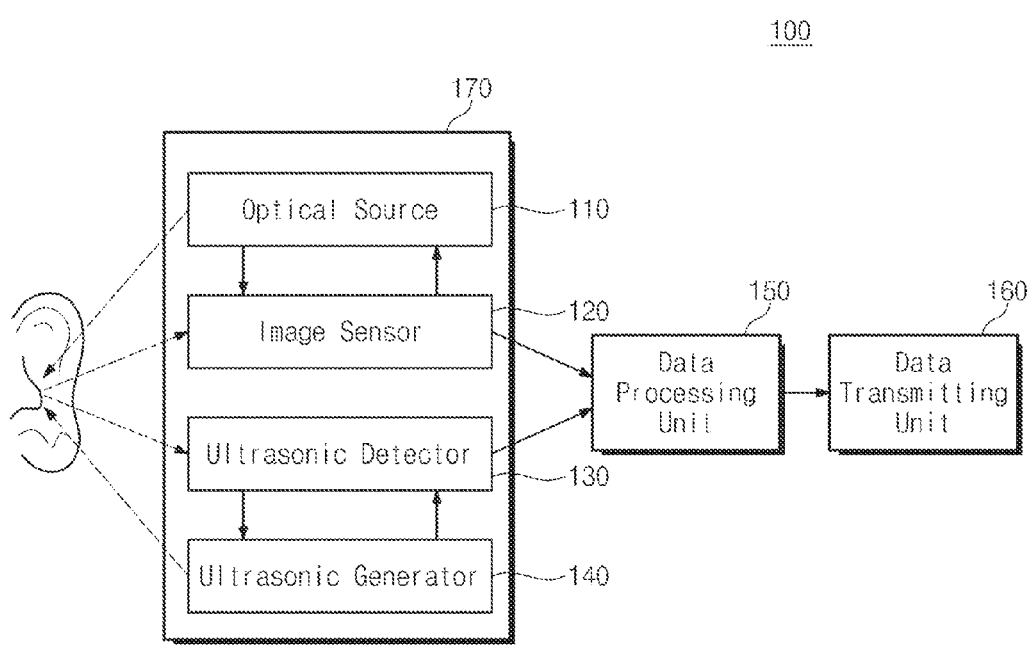
FIG. 4 is a block diagram illustrating a bio-data detection unit of the canal type mini-apparatus according to an embodiment of the present invention.

FIG. 4 is a block diagram illustrating the bio-data detection unit 100 of the canal type mini-apparatus 1000 according to an embodiment of the present invention.

Referring to FIG. 4, the bio-data detection unit 100 may include an image capture unit 170, a data processing unit 150, and a data transmitting unit 160. The image capture unit 170 may include the optical source 110, the image sensor 120, the ultrasonic generator 140, and the ultrasonic detector 130.

The image capture unit 170 takes images of the inner skin of the ear for diagnosing diseases such as tympanitis, tympanum trouble, and jaundice. Still images, videos, or heat distribution images may be obtained using the image sensor 120.

The data processing unit 150 converts images obtained using the image capture unit 170 into transmission signals for sending the transmission signals to the analyzing device 2000 (refer to FIG. 3).

The data transmitting unit 160 transmits the transmission signals to the analyzing device 2000 that can perform image processing.

The optical source 110 emits light so that a clear image can be obtained using the image sensor 120.

The image sensor 120 is used to obtain images of the surface of the inner skin of the ear. A general complementary metal oxide semiconductor (CMOS) image sensor or a charge coupled device (CCD) image sensor may be used as the image sensor 120. If an infrared image sensor is used as the image sensor 120, heat distribution images may be obtained using the image sensor 120.

The ultrasonic generator 140 generates ultrasonic signals to obtain biological images from the surface, inside, and tissues of the inner skin of the ear.

The ultrasonic detector 130 detects ultrasonic waves generated from the ultrasonic generator 140 and reflected from the surface and inside of the inner skin of the ear.

In the embodiment shown in FIG. 4, the image capture unit 170 can capture images by using the optical source 110 and the image sensor 120. In addition, the image capture unit 170 can capture images by generating ultrasonic waves using the ultrasonic generator 140 and detecting the ultrasonic waves using the ultrasonic detector 130. However, alternatively, the image capture unit 170 may include only one of the set of the optical source 110 and the image sensor 120 and the set of the ultrasonic generator 140 and the ultrasonic detector 130.

Figure 5:
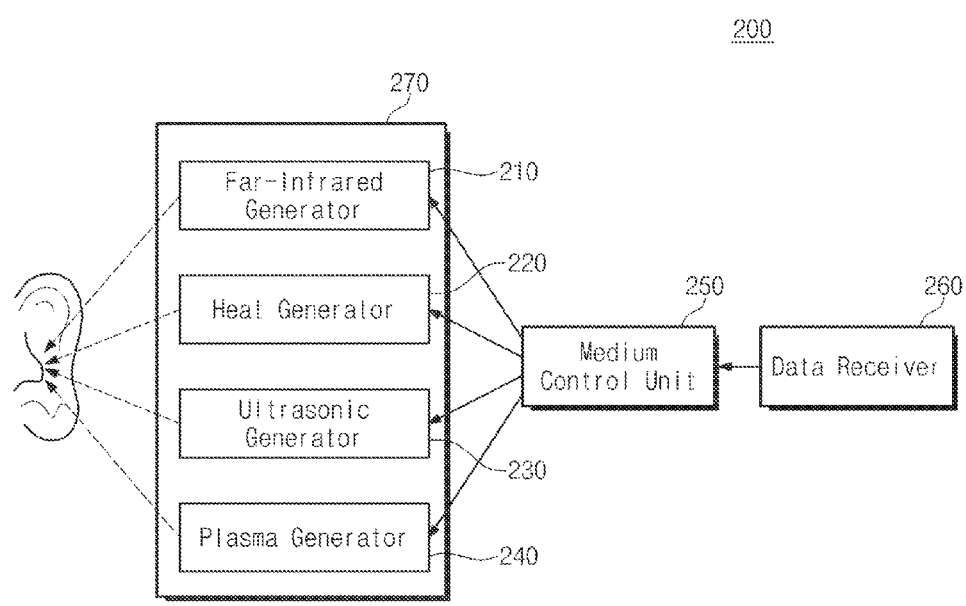
FIG. 5 is a block diagram illustrating a medium injection unit of the canal type mini-apparatus according to an embodiment of the present invention.

FIG. 5 is a block diagram illustrating the medium injection unit 200 of the canal type mini-apparatus 1000 according to an embodiment of the present invention.

Referring to FIG. 5, the medium injection unit 200 may include a medium generating unit 270, a medium control unit 250, and a data receiving unit 260. The medium generating unit 270 may include a far-infrared generator 210, a heat generator 220, an ultrasonic generator 230, and a plasma generator 240.

The medium generating unit 270 generates media such as light, heat, and ultrasonic waves to improve the inner state of the ear suffering from a disease such as tympanitis and dermatitis.

The medium control unit 250 controls the medium generating unit 270 so that a medium can be injected to the ear according to a signal transmitted from the analyzing device 2000 (refer to FIG. 3).

The data receiving unit 260 receives a control signal from the analyzing device 2000 through a wired or wireless communication link.

A general far-infrared treatment device used in hospitals may be fabricated in a small size and may be used as the far-infrared generator 210. The far-infrared generator 210 may be placed in the ear at a position close to the inner skin so as to cure a disease such as dermatitis.

The ultrasonic generator 230 may be the same device as the ultrasonic generator 140 (refer to FIG. 4) of the image capture unit 170. The ultrasonic generator 230 may be used for ultrasonic treatment.

The plasma generator 240 may generate plasma at atmospheric pressure for the purpose of treatment.

As described above, the bio-data detection unit of the canal type mini-apparatus can detect biological data from the inside of an ear for diagnosing a disease, and the medium injection unit can be used to cure a diagnosed disease. Therefore, the degree and development of an ear disease can be determined and cured. In addition, a patient can check the ear disease at home at any time and cure the ear disease so that the health of the patient can be improved.

In addition, since the canal type mini-apparatus is sufficiently compact to be inserted in the ear of a user, the canal type mini-apparatus can be easily carried and connected to a portable analyzing device. Thus, the user can easily check basic biological signals such as temperature, pulse, blood pressure, and electrocardiogram at any place at any time. In addition, the user can easily capture images of the inside of the ear at any place and at any time to check the ear disease such as tympanitis, tympanum trouble, and jaundice, or to determine the degree and development of the ear disease using an analyzing device.

The above-disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A canal type mini-apparatus insertable in an ear, the canal type mini-apparatus comprising:
    a canal body insertable in an ear and comprising at least one of a bio-data detection unit and a medium injection unit at an end thereof, the bio-data detection unit being configured to detect biological data from an inside of the ear for diagnosing a disease, the medium injection unit being configured to generate a medium to the inside of the ear for curing the diagnosed disease; and
    a protrusion body disposed at the other end of the canal body and comprising a data transceiving unit, the data transceiving unit being configured to control the bio-data detection unit and the medium injection unit and transmit/receive a signal to/from an analyzing device,
    wherein when the canal type mini-apparatus is inserted in the ear, at least a portion of the protrusion body protrudes outward from the ear,
    wherein the protrusion body has a socket or adaptor shape for coupling with the canal body.

2. The canal type mini-apparatus of claim 1, wherein the bio-data detection unit is configured to capture an image from an inner skin of the ear for diagnosing at least one of tympanitis, tympanum trouble, and jaundice.

3. The canal type mini-apparatus of claim 2, wherein the bio-data detection unit comprises:
    an image capture unit configured to capture the image of the inner skin of the ear;
    a data processing unit configured to convert the image into a transmission signal; and
    a data transmitting unit configured to transmit the transmission signal to the analyzing device.

4. The canal type mini-apparatus of claim 3, wherein the image capture unit comprises at least one set of a set of an optical source and an image sensor and a set of an ultrasonic generator and an ultrasonic detector.

5. The canal type mini-apparatus of claim 1, wherein the bio-data detection unit is configured to detect a basic biological signal including at least one of temperature, pulse, blood pressure, and electrocardiogram.

6. The canal type mini-apparatus of claim 1, wherein if the analyzing device diagnoses a disease based on biological data detected from the inside of the ear by the bio-data detection unit and transmits a medium-request signal, the medium injection unit generates the medium for curing the disease.

7. The canal type mini-apparatus of claim 1, wherein the medium injection unit comprises:
    a data receiving unit configured to receive a transmission signal providing information about a diagnosed disease from the analyzing device;
    a medium control unit configured to select a medium suitable for curing the diagnosed disease based on the transmission signal; and
    a medium generating unit configured to generate the medium selected by the medium control unit.

8. The canal type mini-apparatus of claim 7, wherein the medium generating unit comprises at least one of a far-infrared generator, a heat generator, an ultrasonic generator, and a plasma generator.

* * * * *